United States Patent
Mosbach et al.

(10) Patent No.: US 6,274,686 B1
(45) Date of Patent: *Aug. 14, 2001

(54) AMIDE CONTAINING MOLECULAR IMPRINTED POLYMERS

(76) Inventors: Klaus Mosbach, Lackalanga 31, S-244 94 Furulund; Cong Yu, Magistratsvägen 550-205 G, S-226 44 Lund, both of (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/866,309

(22) Filed: May 30, 1997

(51) Int. Cl.$^7$ ............................. C08F 20/54; C08F 22/38
(52) U.S. Cl. ................. 526/303.1; 210/656; 210/660; 526/213; 526/215; 526/217; 526/220; 526/236; 526/307.7; 526/335
(58) Field of Search .............................. 526/307.7, 303.1, 526/215, 217, 220, 236, 335, 213

(56) References Cited

U.S. PATENT DOCUMENTS

| | | | |
|---|---|---|---|
| 5,541,342 | 7/1996 | Korhonen et al. | 548/532 |
| 5,630,978 | * 5/1997 | Domb | 264/330 |
| 5,728,296 | 3/1998 | Hjerten et al. | . |

OTHER PUBLICATIONS

C. Yu, K. Mosbach: "Molecular Imprinting Utilizing an Amide Functional Group for Hydrogen Bonding Leading to Highly Efficient Polymers" J. of Organic Chemistry, vol. 62, No. 12, 1997, pp. 4057–4064.

M. Burow, N. Minoura: "Molecular Imprinting: Synthesis of Polymer Particles with Antibody–like Binding Characteristic for Glucose Oxidase:" Biochemical and Biophysical Research Comm., vol. 227, No. 2, 1996, pp. 419–422.

K. Ohkubo, Y. Urata, S. Hirota, Y. Funakoshi, t. Sagawa, S. Usui, K. Yoshinaga: "Catalytic activities of novel L–histidyl group–introduced polymers imprinted by a transition state analogue in the hydrolysis of amino acid esters" J. of Molecular Catalysis A: Chemical, vol. 101, No. 2, Aug. 11, 1995, pp. L111–L114.

K. Ohkubo, Y. Funakoshi, t. Sagawa: "Catalytic activity of a novel water–soluble cross–linked polymer imprinted by a transition–state analogue for the stereoselective hydrolysis of enantiomeric amino acid esters" Polymer, vol. 31, No. 17, 1996, pp. 3993–3995.

O. Ramstrom, L. I. Andersson, K. Mosbach: "Recognition Sites Incorporating Both Pyridinyl and Carboxy Functionalities Prepared by Molecular Imprinting" J. of Organic Chem., vol. 58, No. 26, 1993, pp. 7562–7564.

L. Andersson, B. Sellergren, K. Mosbach: Imprinting of Amino Acid Derivatives in macroporous Polymers: Tetrahedron Letters, vol. 25, No. 45, 1984, pp. 5211–5214.

Beach, J. V. et al: Designed Catalysts. A Synthetic Network Polymer that Catalyzes the Dehydrofluorination of 4–Fluoro–4–(P–Nitrophyenyl)Butan–2–One: J. of Amer Chem Soc., vol. 115, No. 1, Jan. 12, 1994, pp. 379/380.

Shea K. J. et al: Synthesis and Characterization of Highly Cross–Linked Polyacrylamides and Polymethacrylamides. A New class of macroporous Polyamides: Macomolecules vol. 23, No. 21, Oct. 15, 1990, pp. 4497–4507.

K. Mosbach: Molecular Imprinting: Trends in Biochemical Sciences (TIBS), vol. 19, Jan. 1994, pp. 9–14.

K. J. Shea: Molecular Imprinting of Synthetic Network Polymers: the De Novo Synthesis of macromolecular Binding and Catalytic Sites: Trends in Polymer Science, vol. 2, No. 5, May 1994, pp. 166–173).

* cited by examiner

Primary Examiner—Fred Zitomer
(74) Attorney, Agent, or Firm—Morgan & Finnegan, L.L.P

(57) ABSTRACT

This invention relates to molecularly imprinted polymers (MIPs) using an amide as the hydrogen bonding functional group. The amide MIPs made according to this invention exhibited enantiomeric recognition of the imprinted species when evaluated by high performance liquid chromatography (HPLC) even in an aqueous phase. In addition, the amide MIPs demonstrated improved enantiomeric resolution and load capacity.

31 Claims, 6 Drawing Sheets

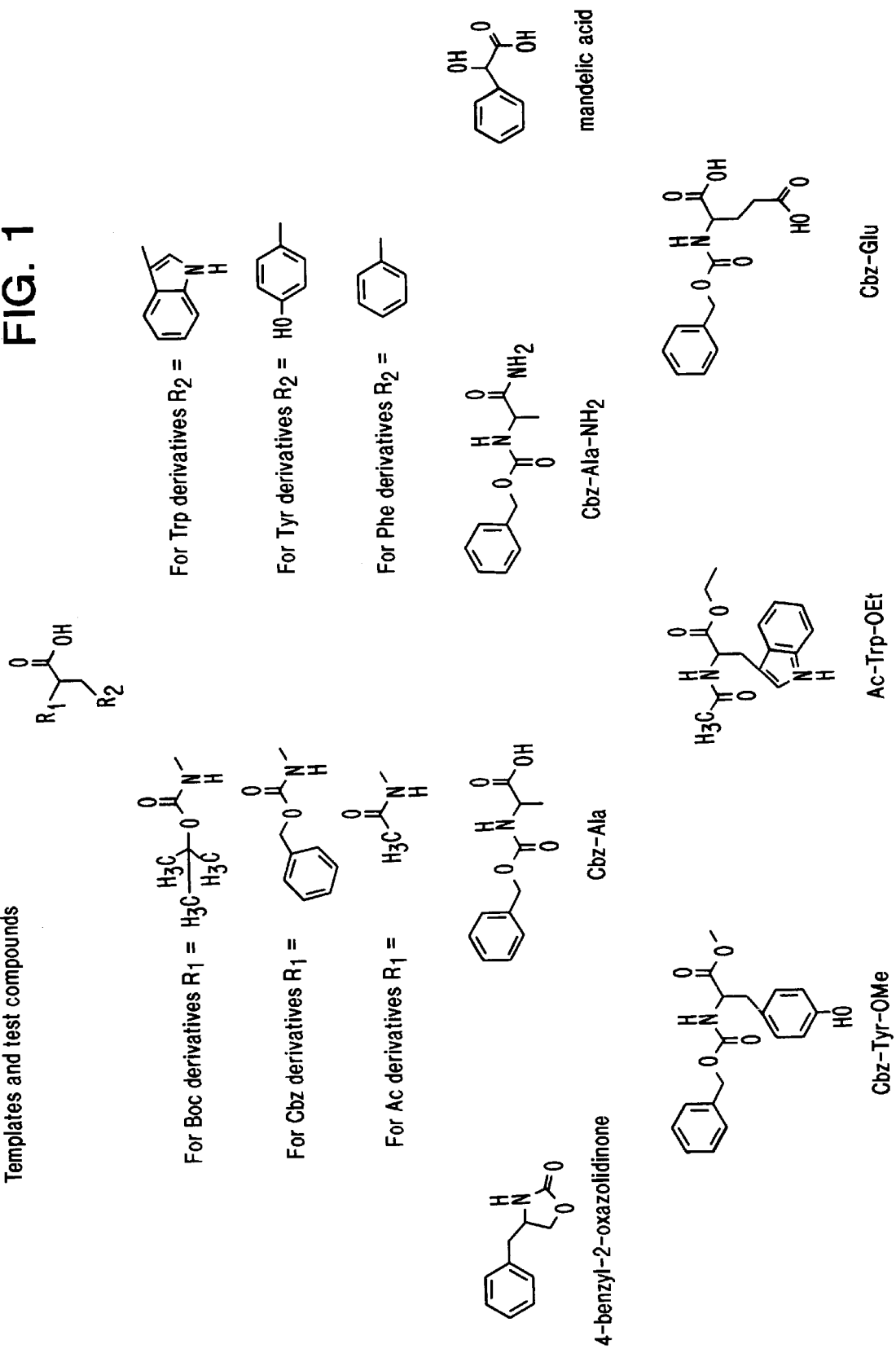

AMIDE CONTAINING MOLECULAR IMPRINTED POLYMERS

FIELD OF THE INVENTION

This invention relates to synthetic molecular imprinted polymers (MIPs), methods of making them and their use as specific binding surfaces. The MIPs of this invention possess amide functional groups which participate in hydrogen bonding during recognition and binding of molecules to the MIP. Accordingly, the improved recognition and binding properties associated with the MIPs of this invention makes them useful, for example, as affinity reagents in separation chemistry, artificial enzymes and artificial receptors.

BACKGROUND OF THE INVENTION

The fabrication of artificial receptors that can achieve recognition at the molecular level is one of the major goals of organic and bio-organic chemistry. Based on the increasing understanding of the basic interactions (hydrogen bonding, ionic interaction, hydrophobic effect, metal chelating, etc.) between molecules and the recognition between substrate-enzyme, antigen-antibody and ligand-receptor, several well known synthetic recognition systems have been developed[1], and newly synthesized receptors are rapidly emerging[2].

Molecular imprinting is a technique for the preparation of such artificial receptors, separation materials of high specificity, artificial enzymes and other synthetic members of a ligand binding pair[3–6]. Molecular imprinted polymer (MIP) materials prepared by molecular imprinting have been successfully used for chiral separation of amino acid derivatives[7], drugs[8], sugar derivatives[9], specific recognition of steroids[10], proteins and protein analogues [11], as antibody and receptor mimics[12], as ion selective absorbents[13] and as enzyme mimics to direct organic reactions[14–17].

Generally, MIPs are prepared by polymerization in a relatively non-polar solvent exhibiting better recognition sites than those prepared using a polar solvent. Better recognition sites are also expected using templates having more noncovalent interacting groups. However, one common problem is that many such compounds are normally not very soluble in nonpolar organic solvents. Because of this, the development of a method for making good MIPs in polar organic solvents is of general interest.

Currently, the carboxyl group is the most commonly used hydrogen bonding functional group. Although it can form strong ionic interactions with basic functional groups, the hydrogen bonding ability of this functional group is not very strong in polar solvents. Often MIPs made in a polar solvent containing carboxyl groups which can only form hydrogen bond interactions with the print molecule exhibit weak recognition, and in some cases no recognition at all[7c,d,18].

Although amide monomers have not been reported as components of MIPs, previous results reported that a polymer imprinted against a template having an amide group instead of an ester group normally gave much better enantiomeric resolution[7a,b,19,20]. In addition, amide monomers have also been used in templates in combination with different functional monomers. For templates having both hydrogen bonding and acidic functional groups, the combination of methyacrylic acid and a basic functional monomer (vinyl pyridine) was shown to give MIPs improved enantiomeric recognition[7d]. One obvious problem with this combination is that the ionic interaction between these two functional monomers might decrease the imprinting efficiency.

U.S. Pat. No. 5,541,342 refers to the preparation of molecular imprints using polymers of L-proline and methacrylic acid amide. The amide group, however, becomes part of the linking group to the proline and is not available to participate in bonding to the print molecule. Rather, as in other prior art MIPS, non-covalent bonding of the print molecule occurs through carboxyl groups, in this case provided by the prolines.

SUMMARY OF THE INVENTION

This invention relates to synthetic amide containing synthetic molecular imprinted co-polymers (MIPs), methods of making them and their use as members of a ligand binding pair. The MIPs of the invention comprise a monomer possessing a free amide group and a cross-linking component. Monomer subunits containing at least one free amide group provide for reversible binding with print molecules to which the MIPs are formed. Following formation of the MIPs, and separation of the print molecules, the MIPs of the invention are capable of specifically binding to certain molecules structurally similar to the print molecules.

The MIPs of the invention are useful as specific binding reagents as a result of their ability to participate in strong non-covalent binding interactions with ligands which fit into the binding site created by the print molecule. The MIPs of the invention are therefore useful in any system dependent on specific molecular recognition such as, for example, separation materials, artificial enzymes, artificial receptors or antibodies.

Another aspect of this invention are MIPs without carboxylic acid groups and the subsequent reduction of non-specific binding.

An object of this invention is to provide MIPs containing free amide groups which are capable of non-covalently binding to print molecules and other structures capable of binding to the binding site created by the print molecule and thus have improved specificity for such ligands.

Another object of this invention is to provide methods of making the MIPs of the invention by using monomers possessing amide rather than carboxyl groups.

Another object of this invention is provide reagents and methods for effecting the separation of enantiomers from racemic mixtures.

Another object of the invention are methods of preparing the MIPs of the this invention.

A still further object of the present invention are MIPs containing a plurality of molecular subunits geometrically configured for selective absorption of a print molecule of interest, and wherein at least one of the subunits contains a free amide group.

A further object of the present invention is providing a print molecule configured copolymer containing free amide groups for reversibly binding.

These and other objects will become more apparent when considered inconjunction with the following detailed

BRIEF DESCRIPTION OF THE FIGURES

FIG. 1 Represents structures of different templates and print molecules (i.e., test compounds) used for formation of MIPs and to assess the recognition of the MIP binding sites.

DETAILED DESCRIPTION OF THE INVENTION

Figure 2A:
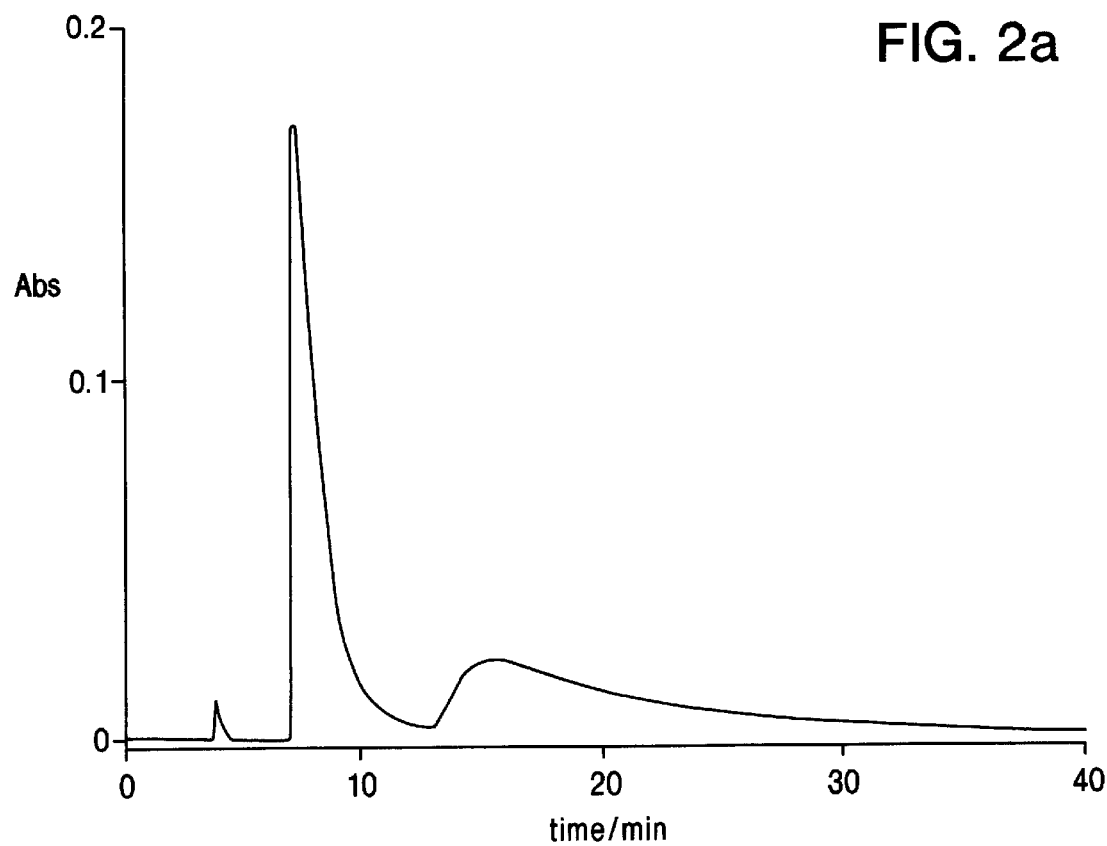
FIG. 2 Comparison of an enantiomeric separation using isocratic or gradient elution. Amide MIP was made against Boc-L-Trp. a).Mobile phase: 0.3% HAc in acetonitrile; flow rate; 1.0 ml/min; 40 μg Boc-D,L-Trp was injected in 20 μl acetonitrile; $k'_D$=0.92, $k'_L$=2.83, α=3.08, $R_1$=1.97. b). Gradient elution, solvent A: acetonitrile, solvent B; acetic acid; 0–6.71 min 0.3% B; 6.71–7.71 min 0.3–7% B, 7.71–22 min 7% B, 22–23 min 7–0.3% B, 23–40 min 0.3% B; flow rate: 1.0 ml/min; 40 μg Boc-D,L-Trp was injected in 20 μl acetonitrile; $k'_L$=2.53, α=2.69, $R_1$=2.51.

This invention provides for the introduction of a new hydrogen bonding functional group, amide groups, into molecularly imprinted polymers via copolymerization of a cross-linker such as, for example, ethylene glycol dimethacrylate (EGDMA) with a functional monomer such as acrylamide in the presence of different templates, or print molecules. Amide and carboxyl groups differ electrostatically, which difference may impart different chemical characteristics in compounds containing them. The significant differences between the dielectric constants and dipole moments of the amide group and the carboxyl group suggest that the amide group may form stronger hydrogen bonds than the carboxyl group. For instance, acetic acid has a dielectric constant value of 6.20, acetamide has a value of 67.6. The dipole moment of acetic acid is 1.70 D, while for acetamide this value is 3.76 D[21]. In a peptide bond, the amide oxygen has 0.42 negative charge and the hydrogen has a 0.20 positive charge. This also suggests that the amide group may form strong hydrogen bonds in water[22].

Strong hydrogen bonding interactions may be formed between the templates and the amide functional groups in a polar organic solvent such as, for example, acetonitrile. The resulting polymers demonstrate significantly improved enantiomeric recognition and load capacity compared to similarly prepared carboxyl MIPS. By using linear gradient elution, peak symmetry and tailing were also significantly improved. The selectivity of amide MIPs depends on the hydrogen bonds formed between the sample molecule and amide groups at the recognition sites of the imprinted polymer, the size and shape of the sample molecule.

Generally, in the present invention MIPs are formed from a plurality of subgroups units, e.g., an amide containing monomer, a cross-liking agent, an optional carboxylic acid containing monomer, and the molecular molecule of interest. Because of noncovalently interaction, the print molecule is readily removed after polymerization thereby forming a formed polymer having predetermined, geometrically configured sites for selective absorption of the molecule or analyte of interest.

The term "free amide group" as used herein means an amide group not covalently bonded to form the co-polymer.

Synthetic molecular imprinted co-polymers of this invention comprise a plurality of molecular subunits, at least one of which comprises a free amide group. Any polymerizable monomer, or combination of monomers, is suitable for use in this invention provided it possess an amide group which remains available for non-covalently binding to the print molecule and thus in the recognition site of the MIP. Examples of such monomers include, but are not limited to acrylamide and methacrylic acid amide. Most preferred is acrylamide.

The other component of the co-polymer is a cross-linking reagent which cross-links the amide containing monomer subunits to form the molecular imprinted co-polymer. An example of a suitable cross-linking reagent includes, but is not limited to ethylene glycol dimethacrylate (EGDMA).

Preparation of the MIPs according to the invention comprises the steps of combining the amide containing monomers with print molecules, preferably, in any suitable polar organic solvent, such as, acetonitrile, chloroform or water. Following non-covalent binding of the amide containing monomers with the print molecules, the cross-linking reagent is added to the reaction to cause polymerization. The components necessary to form the MIPs of the invention will be added in a ratio sufficient to form a specific binding site defined by non-covalent interactions with the print molecule. The molar ratio of print molecule to amide containing monomer to cross-linker of 1:2 to 4:20. Most preferred are ratios of print molecule to amide containing monomer to cross-linker of about 1:2:20 and 1:4:20.

This invention provides a simple protocol for molecular imprinting utilizing non-covalent interactions. The MIPs provided by this invention may be prepared without monomers containing carboxylic groups, therefore allowing for the preparation of synthetic polymers without the excess of charged groups that often can lead to problems of swelling and non-specific binding.

Biological recognition mainly occurs in aqueous systems, it is therefore important to make MIPs capable of recognition in water in order to mimic biomolecules. Because, unlike the carboxyl group, the amide group is not ionizable, the MIPs provided by this invention have a significant advantage for molecular recognition in water.

The results obtained show that an amide is a useful functional group to form strong hydrogen bonds with the template print molecule in polar solvents. Acetonitrile and chloroform are the most commonly used solvents for imprinting. Acetonitrile is much more polar than chloroform, the dielectric constant for acetonitrile being 36.64, while that for chloroform is only 4.81[21]. Previous studies have shown that when an imprint molecule is capable of ionic interactions with the carboxyl monomers, both solvents are good as imprinting solvents. However, when only hydrogen bonding interactions between the imprint molecule and the carboxyl monomers are involved, carboxyl MIPs made in acetonitrile exhibited only very weak enantiomeric recognition[7d] and in some cases no recognition at all[18]. When acetonitrile was used as the imprinting solvent, carboxyl MIPs imprinted against Boc-L-Trp and Cbz-L-Tyr gave only very slight enantiomeric recognition ($\alpha$=2.03, $R_s$=0.16; $\alpha$=1.82, $R^s$=0.3 respectively). When made against Boc-L-Phe, Cbz-L-Phe, or Cbz-L-Ala, no enantiomeric recognition was observed. By contrast, as shown here, most of the amide MIPs made in acetonitrile resulted in good enantiomeric recognition (Table 1–8). The results clearly show that, in acetonitrile, the amide group can form much stronger hydrogen bonds with the templates than the carboxyl group.

In some cases, amide MIPs made in acetonitrile have better enantiomeric recognition than that reported in the literature for carboxyl MIPs made in chloroform. An amide MIP against Cbz-L-Trp gave an $\alpha$ value of 3.68 and an $R^s$ value of 2.24, while the carboxyl MIP made in chloroform gave an $\alpha$ value of 1.67 and an $R^s$ value of only 0.1. For an amide MIP against Boc-L-Trp, the $\alpha$value was 3.68 and the $R^s$ value was 2.24, for the corresponding carboxyl MIP, these two values were 1.90 ad 0.8 respectively[7c].

An amide MIP made against Ac-L-Trp-EOt using acetonitrile as the solvent gave only weak enantiomeric separation, 0.4 $\mu$g of Ac-D,L-Trp-OEt was separated with $\alpha$=1.77 and $R_s$,-0.49. But the made MIP made against the same template using chloroform as the solvent gave much better separation with $\alpha$=1.97 and $R_s$=2.60 (Table 8).

TABLE 8

Chromatographic results for enantiomeric resolution of amide MIPS.

| print molecule | $k'_D$ | $k'_L$ | $\alpha$ | $R_S$ |
|---|---|---|---|---|
| Ac-L-Trp-OEt | 0.14 | 0.25 | 1.77 | 0.49[a] |
|  | 5.74 | 11.30 | 1.97 | 2.60[b] |
| Cbz-L-Glu | 2.56 | 5.10 | 1.99 | 1.54[c] |
| Cbz-L-Ala | 1.88 | 3.72 | 1.98 | 1.58[d] |
| Cbz-L-Ala-NH$_2$ | 0.59 | 1.03 | 1.75 | 1.48[e] |
| D(–)mandelic acid | 2.12 | 3.77 | 1.78 | 1.02[f] |
| S-(–)-4-benzyl-2-oxazolidinone | 1.18 | 1.56 | 1.32 | 1.11[g] |

[a]CH$_3$CN was used as the mobile phase, 0.4 $\mu$g Ac-D,L-Trp-OEt was injected in a total volume of 20 $\mu$l mobile phase. When the mobile phase was changed to CHCl$_3$:heptane (1:1), no separation was observed.
[b]Polymer was made in CHCl$_3$, CHCl$_3$:heptane (1:1) was used as the mobile phase, 10 $\mu$g sample was injected.
[c]3% H$_2$O in CH$_2$CN was used as the mobile phase, 40 $\mu$g sample was injected.
[d]CH$_3$CN was used as the mobile phase, 40 $\mu$g sample was injected.
[e]CH$_3$CN was used as the mobile phase, 20 $\mu$g sample was injected.
[f]0.1% HAc in CH$_3$CN was used as the mobile phase, 20 $\mu$g sample was injected, the flow rate was 0.5 ml/min.
[g]Polymer was made in CHCl$_3$, CHCl$_3$:heptane (3:1) was used as the mobile phase, 10 $\mu$g sample was injected.

Amide MIPs also show much improved capacities in comparison to carboxyl MIPs. For the amide MIP made against Boc-L-Trp, 40 $\mu$g Boc-D,L-Trp can be separated with an $\alpha$value of 3.68 and an $R_s$ value of 2.24, 100 $\mu$g sample can be separated with an $\alpha$ value of 2.88 and an $R_s$ value of 1.39, 500 $\mu$g sample can be separated with an a value of 1.47 and an $R_1$ value of 0.64. For the corresponding carboxyl MIP, 40 $\mu$g Boc-D,L-Trp gave an $\alpha$ value of 2.03 and an $R_s$ value of 0.16. Thus, in this case, the amide MIP has a capacity at least 10 times greater than the carboxyl MIP.

Since most of the templates used to construct the MIPs have a free carboxyl group, it was decided to imprint two templates without free carboxyl groups (Ac-L-Trp-OEt and Cbz-Ala-NH$_2$). Polymers imprinted with both compounds exhibited good enantiomeric recognition, showing that a free carboxyl group is not obligatory for the template (Table 8).

Two non-amino acid derivatives, S-(–)-4-benzyl-2-oxazolidinone and D(–)mandelic acid were also imprinted. Both of the resulting polymers exhibited good enantiomeric recognition (Table 8). This demonstrates that compounds other than amino acid derivatives can also be used as templates.

Linear Gradient Elution.

Figure 2B:
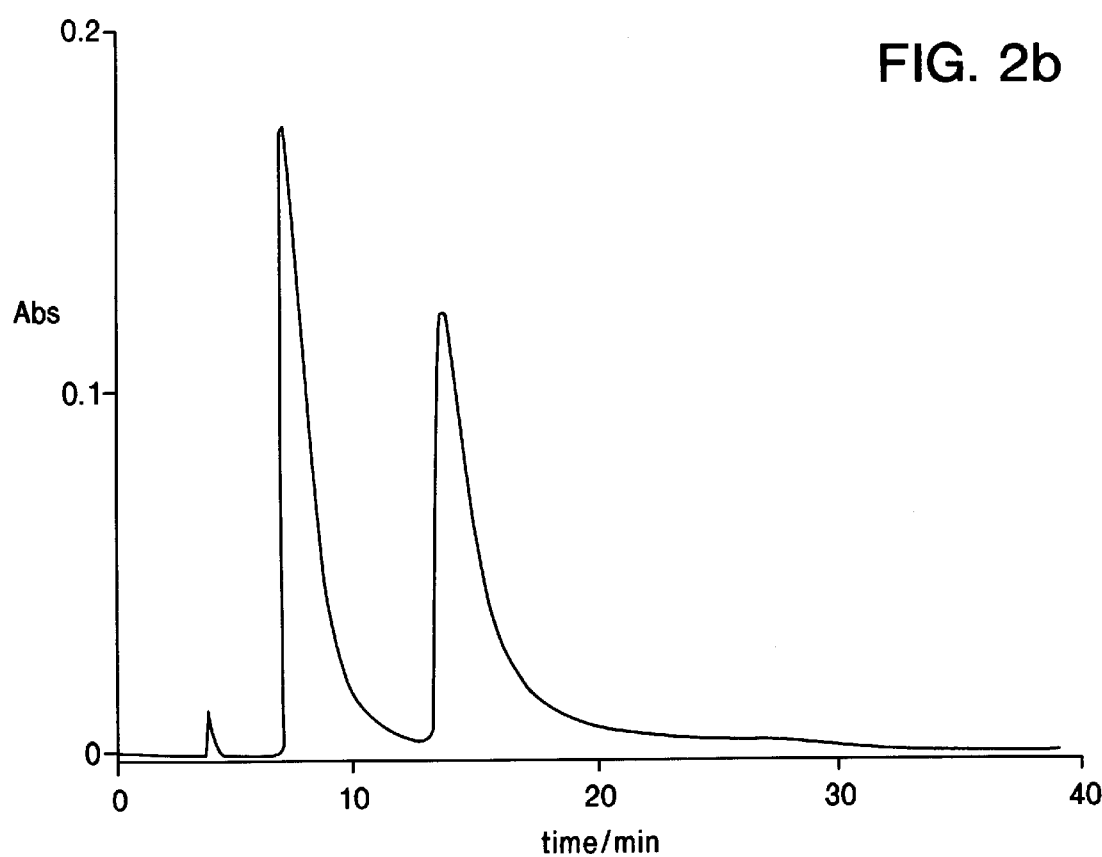

When using HPLC to analyze MIPS, one common problem is that the more retarded peak is normally very broad, highly asymmetric, and tails badly. Tailing can considerably increase the time needed to complete one analysis and bad peak symmetry makes it difficult to measure HPLC chromatogram parameters accurately. The poor resolution is probably due to the fact that imprinting normally cannot create homogenous binding sites and that there is a distribution of binding sites with different affinities for the sample molecule[12]. Slow mass transfer maybe also constructed to the poor resolution. In order to distinguish the sample peak from the noise, a competing ligand (like acetic acid) must sometimes be added to the mobile phase. Unfortunately, this may considerably reduce the enantiomeric separation. Gradient elution has previously been used with a carboxyl MIP with marginal improvements in peak symmetry[7b]. Results for amide MIPs show that by using linear gradient elution, the peak symmetry is greatly improved, the tailing problem is significantly reduced, and the time needed for one analysis is shortened. The resolution is also increased due to the increase in peak symmetry, although with some decrease in the separation value (FIG. 2).

The Selectivity of Amide MIPS.

Most investigations of MIPs have concentrated on enantiomeric recognition, whereas investigations concerning the various structures is of ligands have not been focused on to the same degree. In our selectivity study, three kinds of amino acid derivatives (tryptophan, tyrosine and phenylalanine) were selected and comparisons were made of their retentions by different MIPs in high performance liquid chromatography (HPLC) in order to reveal how MIPs recognized different molecules with specificity (FIG. 1).

Three amino acid derivatives, namely tryptophan, tyrosine and phenylalanine derivatives were chosen for the selectivity study. The similar structures of these derivatives provides a good test of the polymers' selectivity. The changes in enantiomeric recognition with the side chain, the protecting group and the esterification of the carboxyl group also offer a good opportunity to identify and characterize the factors that determine the selectivity of MIPs (Table 1–7).

TABLE 1

Chromatographic results for enantiomeric resolution of structurally related compounds on an amide MIP prepared using Boc-L-Trp as the template

| test compound | $k'_D$ | $k'_L$ | α | $R_I$ |
|---|---|---|---|---|
| Boc-Trp | 1.44 | 5.30 | 3.68 | 2.24 |
| Boc-Tyr | 1.51 | 2.46 | 1.63 | 0.93 |
| Boc-Phe | 0.78 | 1.23 | 1.58 | 0.81 |
| Cbz-Trp | 2.04 | 3.79 | 1.86 | 1.27 |
| Cbz-Tyr | 2.50 | 2.95 | 1.18 | 0.26 |
| Cbz-Phe | 1.23 | 1.14 | 1.15 | 0.15 |
| Ac-Trp | 1.77 | 2.41 | 1.36 | 0.56 |
| Ac-Tyr | 2.07 | 2.07 | — | — |
| Ac-Phe | 1.06 | 1.06 | — | — |
| Ac-Trp-OEt | 0.13 | 0.13 | — | — |
| Boc-Tyr-OMe | 0.12 | 0.12 | — | — |

TABLE 2

Chromatographic results for enantiomeric resolution of structurally related compounds on an amide MIP prepared using Boc-L-Tyr as the template.

| test compound | $k'_D$ | $k'_L$ | α | $R_I$ |
|---|---|---|---|---|
| Boc-Trp | 2.04 | 2.86 | 1.40 | 0.94 |
| Boc-Tyr | 3.48 | 9.92 | 2.86 | 2.63 |
| Boc-Phe | 1.31 | 2.19 | 1.68 | 1.59 |
| Cbz-Trp | 3.08 | 3.54 | 1.15 | 0.28 |
| Cbz-Tyr | 5.44 | 9.46 | 1.74 | 1.46 |
| Cbz-Phe | 2.02 | 2.49 | 1.24 | 0.61 |
| Ac-Trp | 3.25 | 3.25 | — | — |
| Ac-Tyr | 5.06 | 6.61 | 1.31 | 0.62 |
| Ac-Phe[a] | 1.83 | 1.83 | — | — |
| Ac-Trp-OEt | 0.10 | 0.10 | — | — |
| Boc-Tyr-OMe | 0.25 | 0.25 | — | — |

[a]Injection 1/10 amount of sample gave $k'_D$ = 1.74, $k'_L$ = 2.06, α = 1.18, $R_I$ = 0.26

TABLE 3

Chromatographic results for enantiomeric resolution of structurally related compounds on an amide MIP prepared using Boc-L-Phe as the template.

| test compound | $k'_D$ | $k'_L$ | α | $R_I$ |
|---|---|---|---|---|
| Boc-Trp | 1.70 | 2.33 | 1.37 | 0.73 |
| Boc-Tyr | 2.44 | 3.93 | 1.62 | 1.14 |
| Boc-Phe | 1.18 | 2.38 | 2.03 | 1.73 |
| Cbz-Trp | 2.63 | 2.90 | 1.11 | 0.12 |
| Cbz-Tyr | 3.77 | 4.99 | 1.19 | 0.35 |
| Cbz-Phe | 1.81 | 2.39 | 1.33 | 0.69 |
| Ac-Trp | 2.59 | 2.59 | — | — |
| Ac-Tyr | 3.90 | 3.90 | — | — |
| Ac-Phe | 1.55 | 1.69 | 1.10 | 0.14 |
| Ac-Trp-OEt | 0.16 | 0.16 | — | — |
| Boc-Tyr-OMe | 0.19 | 0.19 | — | — |

TABLE 4

Chromatographic results for enantiomeric resolution of structurally related compounds on an amide MIP prepared using Cbz-L-Trp as the template.

| test compound | $k'_D$ | $k'_L$ | α | $R_I$ |
|---|---|---|---|---|
| Boc-Trp | 1.08 | 1.83 | 1.69 | 0.65 |
| Boc-Tyr[a] | 1.22 | 1.22 | — | — |
| Boc-Phe[b] | 0.75 | 0.75 | — | — |
| Cbz-Trp | 2.06 | 8.23 | 4.00 | 1.88 |
| Cbz-Tyr | 2.02 | 3.60 | 1.78 | 0.77 |
| Cbz-Phe | 1.19 | 1.98 | 1.66 | 0.74 |
| Ac-Trp | 1.50 | 2.61 | 1.74 | 0.72 |
| Ac-Tyr[c] | 1.77 | 1.77 | — | — |
| Ac-Phe[d] | 0.99 | 0.99 | — | — |
| Ac-Trp-OEt | 0.21 | 0.21 | — | — |
| Boc-Tyr-OMe | 0.16 | 0.16 | — | — |

[a]Injection 1/10 amount of sample gave $k'_D$ = 1.34, $k'_L$ = 1.84, α = 1.37, $R_I$ = 0.14
[b]Injection 1/10 amount of sample gave $k'_D$ = 0.73, $k'_L$ = 0.92, α = 1.26, $R_I$ = 0.10
[c]Injection 1/10 amount of sample gave $k'_D$ = 2.09, $k'_L$ = 2.72, α = 1.30, $R_I$ = 0.12
[d]Injection 1/10 amount of sample gave $k'_D$ = 1.23, $k'_L$ = 1.50, α = 1.22, $R_I$ = 0.08

TABLE 5

Chromatographic results for enantiomeric resolution of structurally related compounds on an amide MIP prepared using Cbz-L-Tyr as the template.

| test compound | $k'_D$ | $k'_L$ | α | $R_I$ |
|---|---|---|---|---|
| Boc-Trp | 2.28 | 2.56 | 1.13 | 0.08 |
| Boc-Tyr | 3.54 | 5.68 | 1.60 | 1.15 |
| Boc-Phe | 1.25 | 1.50 | 1.20 | 0.33 |
| Cbz-Trp | 3.53 | 5.26 | 1.50 | 0.96 |
| Cbz-Tyr | 6.80 | 24.6 | 3.62 | 2.52 |
| Cbz-Phe | 2.28 | 4.32 | 1.90 | 1.68 |
| Ac-Trp[a] | 3.55 | 3.55 | — | — |
| Ac-Tyr | 5.72 | 8.93 | 1.56 | 1.08 |
| Ac-Phe | 1.93 | 2.24 | 1.16 | 8.31 |
| Ac-Trp-OEt | 0.19 | 0.19 | — | — |
| Boc-Tyr-OMe | 0.24 | 0.24 | — | — |

[a]Injection 1/10 amount of sample gave $k'_D$ = 4.26, $k'_L$ = 5.52, α = 1.29, a shoulder peak.

TABLE 6

Chromatographic results for enantiomeric resolution of structurally related compounds on an amide MIP prepared using Cbz-L-Phe as the template

| test compound | $k'_D$ | $k'_L$ | α | $R_I$ |
|---|---|---|---|---|
| Boc-Trp | 2.09 | 2.09 | — | — |
| Boc-Tyr | 2.70 | 3.08 | 1.15 | 0.17 |
| Boc-Phe | 1.25 | 1.60 | 1.29 | 0.52 |
| Cbz-Trp | 3.39 | 4.87 | 1.44 | 0.62 |
| Cbz-Tyr | 4.54 | 7.80 | 1.72 | 0.94 |
| Cbz-Phe | 2.39 | 5.64 | 2.36 | 1.58 |
| Ac-Trp | 3.15 | 3.15 | — | — |
| Ac-Tyr | 4.56 | 5.02 | 1.10 | 0.10 |
| Ac-Phe | 1.89 | 2.30 | 1.22 | 0.37 |
| Ac-Trp-OEt | 0.18 | 0.18 | — | — |
| Boc-Tyr-OMe | 0.21 | 0.21 | — | — |

TABLE 7

Chromatographic results for enantiomeric resolution of structurally related compounds on an amide MIP prepared using Ac-L-Trp as the template.

| test compound | $k'_D$ | $k'_L$ | α | $R_I$ |
|---|---|---|---|---|
| Boc-Trp | 1.09 | 1.25 | 1.16 | 0.12 |
| Boc-Tyr | 1.27 | 1.27 | — | — |
| Boc-Phe | 0.66 | 0.66 | — | — |
| Cbz-Trp | 1.76 | 2.64 | 1.50 | 0.60 |
| Cbz-Tyr[a] | 2.15 | 2.15 | — | — |
| Cbz-Phe | 1.16 | 1.16 | — | — |
| Ac-Trp | 1.73 | 5.61 | 3.24 | 2.02 |
| Ac-Tyr | 2.01 | 3.09 | 1.54 | 0.70 |
| Ac-Phe[a] | 0.95 | 1.41 | 1.49 | 0.58 |
| Ac-Trp-OEt | 0.11 | 0.11 | — | — |
| Boc-Tyr-OMe | 0.11 | 0.11 | — | — |

[a]Injection 1/10 amount of sample gave $k'_D = 3.62$, $k'_{L\ =\ 4.18}$, α = 1.16, a shoulder peak.

Figure 3A:
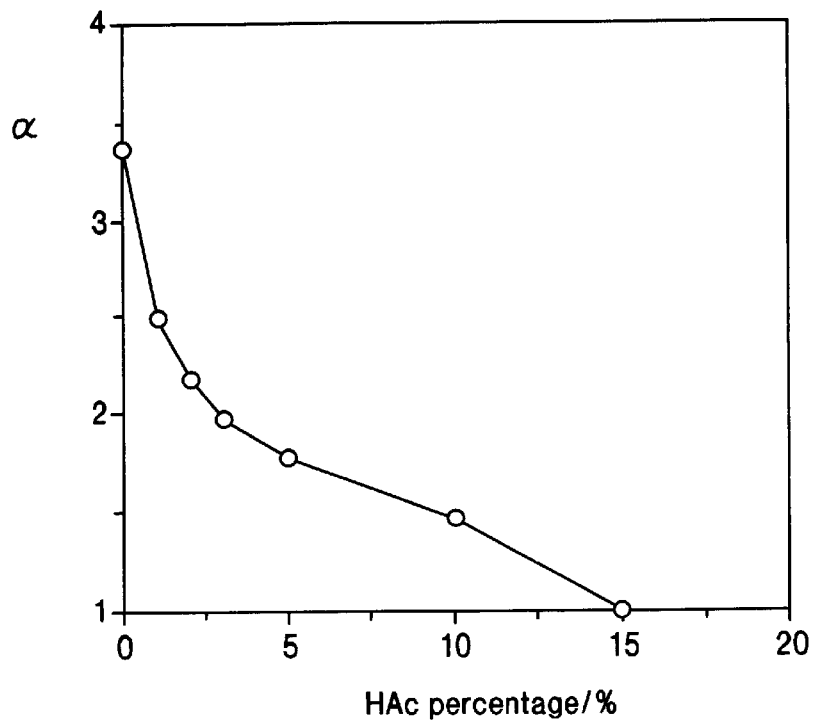
FIG. 3 Enantiomeric recognition (α and $R_2$) versus acetic acid concentration in the mobile phase. Amide MIP was made against Boc-L-Trp. Mobile phase: acetonitrile-acetic acid, flow rate: 1.0 ml/min, 40 μg Boc-D,L-Trp was injected in 20 μl acetonitrile.
Figure 3B:
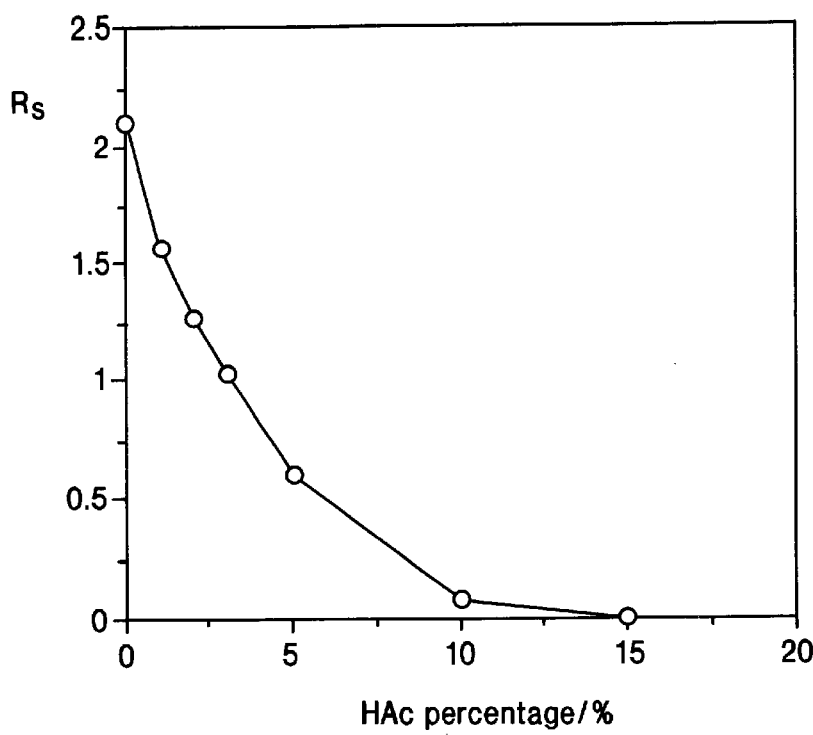

The amide functional group copolymerized into the polymer matrix is the main factor responsible for the enantiomeric recognition. For the amide MIP made against Boc-L-Trp, addition of a competing ligand such as acetic acid in the reaction dramatically reduced the enantiomeric recognition (FIG. 3). When 15 percent acetic acid was used, no enantiomeric separation was observed. This is because acetic acid competed with the sample molecule for the amide hydrogen bonding functional group and reduced the possibility of hydrogen bonding interactions between the sample molecule and the amide group at the recognition sites.

For any enantiomeric recognition, at least three of the four groups around the chiral center must be specifically recognized. For amino acid derivatives, these three groups are the carboxyl group, the amino protecting group and the side chain.

EXAMPLES

Materials and Methods

Amino acid derivatives were obtained from Sigma Chemical Co. (St. Louis, Mo.), Nova Biochem Läufelfingen, Switzerland) or Bachem (Bubendorf, Switzerland). Methacrylic acid and ethylene glycol dimethacrylate (EGDMA) were from E. Merck (Darmstadt, Germany. 2,2'-Azobisisobutyronitrile (AIBN) was from Janssen Chernica (Beerse, Belgium). Acrylamide was from Bio-Rad (Richmond, Calif.). Acetonitrile and chloroform were of HPLC grade.

Polymer Synthesis.

Polymers were prepared using acrylamide as the functional monomer and EGDMA as the crosslinker. The molar ratio of print molecule to functional monomer to cross-linker was 1:4:20 except for S-(−)-4-benzyl-2-oxazolidinone. Due to there being less hydrogen bonding sites available on this template, a molar ratio of 1:2:20 was used instead. Generally a polymer was synthesized using 10 grams EGDMA, 100 mg AIBN (the free radical initiator), and the correct amounts of acrylamide and template. The mixture was dissolved in 15 ml acetonitrile (or chloroform for S-(−)-4-benzyl-2-oxaolidinone and one amide MIP made against Ac-L-Trp-OEt), degassed in a sonicating water bath, saturated with nitrogen for 5 minutes, and polymerized under UV irradiation (366 nm) at 4° C. for 24 hours. The polymer was then ground in a mechanical mortar (Retsch, Haan, Germany), sieved through a 25-μm sieve and fines were removed by repeated sedimentation in acetone.

HPLC Analysis.

After sedimentation, particles were suspended in acetone and slurry packed into 250 mm×4.6 mm I.D. stainless-steel columns at 30 MPa using an air-driven fluid pump and acetone as solvent. An average of 1.47g polymer can be packed into the column under these conditions (21 different experiments). The column was washed on-line with methanol:acetic acid (9:1, v/v) until a stable baseline was achieved.

Generally, within the detection limit, the mobile phase was chosen to give good enantiomeric separation in a reasonable period of time. For the selectivity study, pure acetonitrile was used as the mobile phase. Although in several cases, especially for tyrosine (Tyr) derivatives, the retention times were very long, and this made HPLC analyses quite time consuming, no competing solvent like acetic acid was added to the mobile phase to reduce the retentions. Changing the mobile phase can change the retention time, the separation factor and the resolution value considerably, and this would invalidate the comparison between the different polymers.

For all the HPLC analyses made in this investigation, unless specified, normally 40 μg sample dissolved in 20 μl acetonitrile was injected and analyzed isocratically at a flow rate of 1.0 ml/min using acetonitrile as the mobile phase. For the compounds analyzed in the selectivity study, if one could not be separated by a particular amide MIP, normally 1/10 amount of sample was also analyzed, the result is given as a footnote if it was separated.

Acetone was used as the void marker. Capacity factors ($k'_D$ and $k'_L$), separation factors (α), resolutions ($R_1$) and plate numbers (N) were all calculated according to standard chromatographic theory[21]. For instance, $k'_D=(t_D-t_O)/t_O$, $k'_L=(t_L-t_O)/t_O$, $α=k'_L/k'_D$, $t_D$ is the retention time of the D enantiomer, $t_L$ is the retention time of the L enantiomer, $t_O$ is the retention time of the void. The plate number (N) for acetone for the amide MIP made against Boc-L-Trp was determined to be 1508.

Figure 4A:
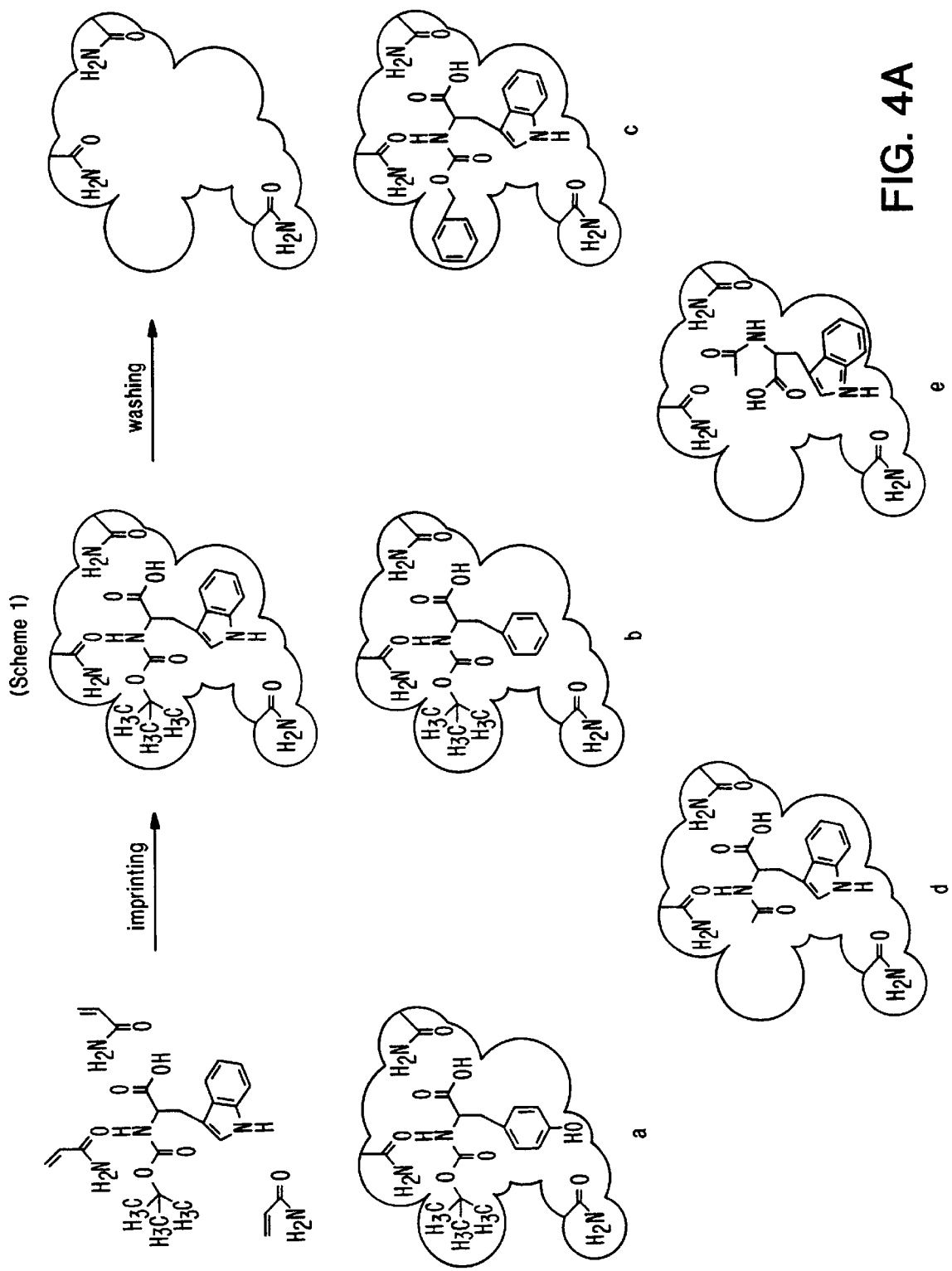
FIGS. 4A, 4B, 4C FIG. 4A (Scheme 1, a–e), 4B (Scheme 2, a–c), and 4C (Scheme 3, a–b) illustrate MIP formation. The ability of the MIP to bind other structures is illustrated in panels a–e of scheme 1, a–c of scheme 2 and a–b of scheme 3.
Figure 4B:
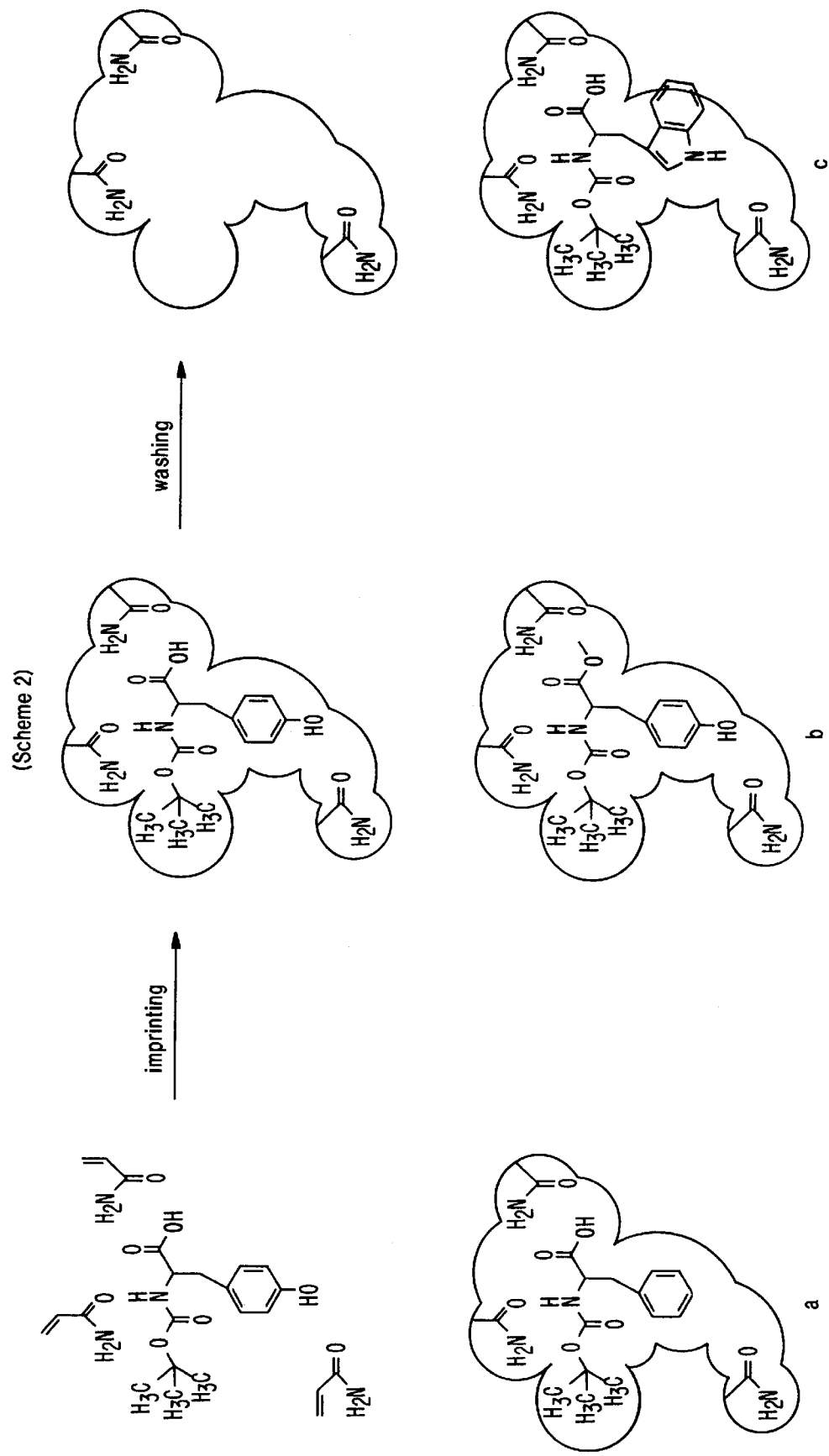
Figure 4C:
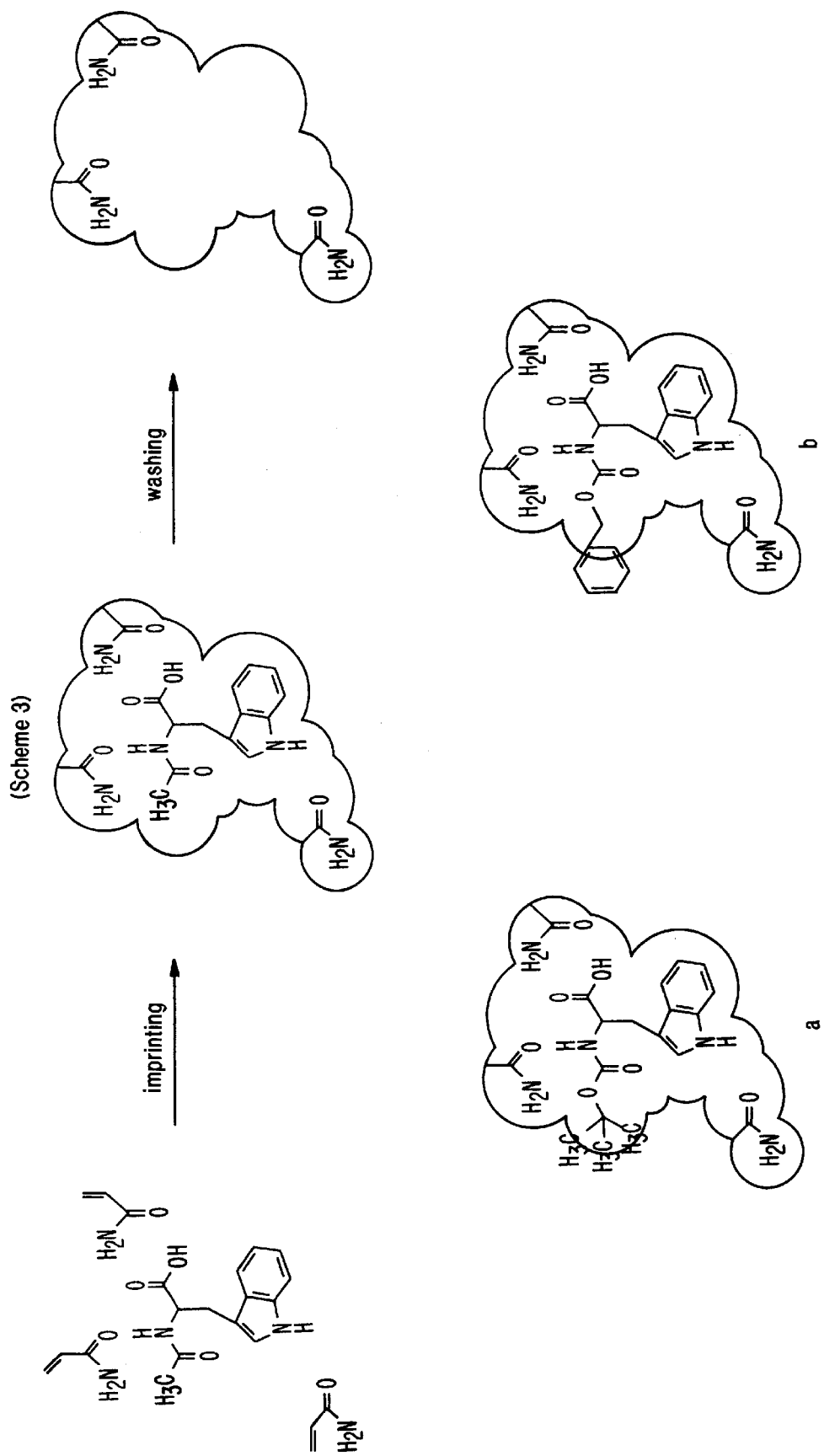

It is believed that prior to polymerization, a complex between the free carboxyl group of the templates and the amide group of the monomer is formed FIGS. 4A–4C (Scheme 1–3). Thus, esterification of the free carboxyl group completely prevents the formation of hydrogen bonds between the carboxyl group and the amide group of the polymer FIG. 4B (Scheme 2b). Neither of the two esters, Ac-D,L-Trp-OEt or Boc-D,L-Tyr-OMe, could be separated by the MIPs made against Ac-L-Trp and Boc-L-Tyr was 0.8 μg, this was only 2 percent of the amount of sample normally injected, and no enantiomeric recognition was observed. In fact, the ester enantiomers were barely retarded.

Similarly, none of the enantiomers except Ac-D,L-Trp-OEt could be separated by the amide MIP made against Ac-L-Trp-OEt.

The protecting groups (Acetyl, Boc and Cbz groups) are all capable of forming hydrogen bonds. The acetyl group itself is an amide. Since the template, S-(−)-4-benzyl-2-oxazolidonone possesses only a carbamate group, it could be imprinted and gave good enantiomeric recognition, so the carbamate group is clearly capable of forming hydrogen bonds. Both Boc and Cbz groups have a carbamate functional group. The difference between these three groups is their size, the acetyl group is much smaller than the other two. Also, the Cbz group is a flat structure, the Boc group is more three dimensional.

For all the amide MIPs made against Trp, Tyr and Phe derivatives, compounds with the same protecting group as the template were always better separated than compounds with different protecting groups. Better separations were observed for Cbz derivatives on amide MIPs made against Boc derivatives than for Boc derivatives on amide MIP made against Cbz derivatives. This is because that the Boc group has a more three dimensional structure, so the cavity created by imprinting the Boc group could accommodate the Cbz group better than the cavity created by imprinting the Cbz group accommodated the Boc group FIG. 4A (Scheme 1c). For the amide MIP made against Ac-L-Trp, the relatively poor separation of the Boc and the Cbz derivatives may be attributed to the small size of the acetyl group compared with the Boc and FIG. 4C Cbz groups (Scheme 3). In this case also, Cbz-D,L-Trp was better separated than Boc-D,L-Trp. The results show that except for the amide MIP made against Ac-L-Trp, acetyl derivatives were generally only poorly separated by other amide MIPs. This may be due to the small size of the acetyl group. Besides the "correct" interaction with the recognition sites, acetyl derivatives could more easily fit "incorrectly" and form stronger non-specific interactions, for instance between the acetyl group and the amide that should interact with the free carboxyl group, making the separation less effective FIG. 4A (Scheme 1d,e).

The side chains of tryptophan and tyrosine can form hydrogen bonds with the amide group while the functional group of phenylalanine cannot. This is supported by the fact that the D-enantiomers, the capacity factors of the Trp and Tyr derivatives are always larger than those of the Phe derivatives, indicating that there are additional non-specific interactions. The phenyl group and the hydroxyphenyl group are quite similar in size, the indole group of tryptophan on the other hand is much larger.

For amide MIPs imprinted against Trp derivatives, the polymers always gave better separation for Tyr derivatives than for Phe derivatives. This is because the Tyr derivatives could hydrogen bond with the amide group in the cavity created by the indole group FIG. 4A (Scheme 1a,b). However, MIPs made against Tyr derivatives exhibited better separation of Phe derivatives than Trp derivatives, and amide MIPs made against Phe derivatives exhibited better separation of Tyr derivatives than Trp derivatives. This is because the cavity created by the hydroxyphenyl group or the phenyl group was not big enough to accommodate the indole ring readily FIG. 4B (Scheme 2a,c). Amide MIPs made against Phe derivatives exhibited better selectivity for Phe derivatives exhibited better selectivity for Phe derivatives than for Tyr derivatives. Thus, a single hydroxy group can clearly contribute to the recognition exhibited by amide MIPs.

For templates with more hydrogen bonding sites available, the MIPs normally showed better enantiomeric recognition of the enantiomers of the template. Amide MIPs made against tryptophan and tyrosine derivatives always gave better enantiomeric recognition of the print compounds than amide MIPs made against phenylalanine derivatives.

Besides all the above discussions about selectivity, perhaps the most obvious demonstration of the selectivity of all the amide MIPs is that the racemate of the print molecule was always better separated than any other racemic pair.

Enantiomeric Recognition in Water.

Amide MIPs are also capable of demonstrating very good enantiomeric recognition in water. For the amide MIP made against Boc-L-Trp, when the molecule phase was chosen to be water:acetonitrile (7:3), 10 mM glycine buffer, pH=3.0, 10 μg Boc-D, L-Trp was separated with $\alpha=1.74$ and $R_{1,}=2.15$. We believe that hydrophobic effects contribute mainly in recognition in aqueous media.

While a number of embodiments of this invention have been described, it is apparent that the basic constructions can be altered to provide embodiments which utilize the methods and teaching of this invention. Therefore, it will be appreciated that the scope of this invention is defined by the claims appended hereto rather than by the specific embodiments which have been presented hereinbefore by way of example.

The following publications are incorporated by reference in their entirety.

References (1) (a) Cram, D. *Angew. Chem. Int. Ed. Engl.* 1988, 27, 1009. (b) Pedersen, C. J. *Angew. Chem. Int. Ed. Engl.* 1988, 27, 1021. (c) Lehn, J. M. *Angew. Chem. Int. Ed. Engl.* 1988, 27, 89. (d) Rebek, J. *Acc. Chem. Res.* 1990, 23, 399. (e) Schneider, H. J. *Angew. Chem. Int. Ed. Engl.* 1991, 30, 1417. (f) Wenz, G. *Angew. Chem. Int. Ed. Engl.* 1994, 33, 803.

(2) (a) Kobuke, Y.; Kokubo, K.; Munakata, M. *J. Am. Chem. Soc.* 1995, 117, 12751. (b) Granados, A.; de Rossi, R. H. *J. Am. Chem. Soc.* 1995, 117, 3690. (c) Kuroda, Y.; Kato, Y.; Higashioji, T.; Hasegawa, J.-Y.; Kawanami, S; Takahashi, M.; Shiraishi, N.; Tanabe, K.; Ogoshi, H. *J. Am. Chem. Soc.* 1995, 117, 10950. (d) Bonar-Law, R. P.; Sanders, J. K. M. *J. Am. Chem. Soc.* 1995, 117, 259. (e) Famulok, M. *J. Am. Chem. Soc.* 1994, 116, 1698.

(3) (a) Mosback, K. *TIBS.* 1994, 19, 9. (b) Ansell, R. J.; Mosback, K. *Pharmaceutical News*, 1996, 3, 16. (c) Mosbach, K.; Ramström, O. *Bio/technology* 1996, 14, 163.

(4) Wulff, G. *Angew Chem. Int. Ed. Engl.* 1995, 34, 1812.

(5) Shea, K. J. *Trends Polym. Sci.* 1994, 2, 166.

(6) Vidyasankar, S.; Arnold, F. H. *Curr. Opin. Biotechnol.* 1995, 6, 218.

(7) (a) Sellergren, B.; Lepistö, M.; Mosbach, K. *J. Am. Chem. Soc.* 1988, 110, 5843. (b) Andersson, L. I.; O'Shannessy, D. J.; Mosbach, K. *J. Chromatogr.* 1990, 513, 167. (c) Andersson, L. I.; Mosbach, K. *J. Chromatogr.* 1990, 516, 313. (d) Ramstrbm, 0.; Andersson, L. I.; Mosbach, K. *J. Org. Chem.* 1993, 58, 7562.

(8) (a) Fischer, L.; Muller, R.; Ekberg, B.; Mosbach, K. *J. Am. Chem. Soc.* 1991, 113, 9358. (b) Kempe, M.; Mosbach, K. *J. Chromatogr.* 1994, 664, 276.

(9) (a) Wulff, G.; Haarer, J. *Markromol. Chem.*, 1991, 192, 1329. (b) Mayes, A. G.; Andersson, L. I.; Mosbach, K. *Anal. Biochem.* 1994, 222, 482.

(10) Whitcombe, M. J.; Rodriguez, M. E.; Villar, P.; Vulfson, E. N. *J. Am. Chem. Soc.* 1995, 117, 7105.

(11) (a) Mallik, S.; Johnson, R. D.; Arnold, F. H.; *J. Am. Chem. Soc.* 1995, 117, 122751. (b) Kempe, M.; Glad, M.; Mosbach, K. *J. Mol. Recogn.* 1995, 8, 35.

(12) (a) Vlatakis, G.; Andersoon, L. I.; Muller, R.; Mosbach, K. *Nature* 1993, 361, 645. (b) Anderson, L. I.; Muller, R.; Vlatakis, G.; Mosbach, K. *Proc. Natl. Acad. Sci. USA* 1995, 92, 478.
(13) Rosatzin, T.; Andersson, L.I.; Simon, W.; Mosbach, K. J. *J. Chem. Soc. Perkin Trans.* 2 1991, 1261.
(14) (a) Stahl, M.; Jeppsson-Wilstrand, U.; Mansson, M.-O; *J. Am. Chem. Soc.* 1991, 113, 9366. (b) Mingarro, I.; Abad, C.; Braco, L.; *Proc. Natl. Acad. Sci. USA* 1995, 92, 3308.
(15) Bystrom, S. E.; Borje, A.; Akermark, B. *J. Am. Chem. Soc.* 1993, 115, 2081.
(16) Robinson, D. K.; Mosbach, K. *J. Chem. Soc. Chem. Commun.* 1989, 14, 969.
(17) Beach, J. V.; Shea, K. J. *J. Am. Chem. Soc.* 1994, 116, 379.
(18) Kempe, M. Ph.D. thesis, University of Lund, 1994, p.44.
(19) Andersoon, L.; Sellergen, B., Mosbach, K. *Tetrahedron Lett.* 1984, 25, 5211.
(20) Sellergen, B.; Ekberg, B.; Mosbach, K. *J. Chromatogr.* 1985, 347, 1.
(21) Lide, D. R. *CRC Handbook of Chemistry and Physics*; CRC Press; Boca Raton, 1994, p.6–1515, 9–42.
(22) Creighton, T. E. *PROTEINS structure and Molecular Properties*; W. H. Freeman: New York, 1993, p.145.
(23) Poole, C. F.; Schutte, S. A. *Contemporary practice of chromatography*; Elsevier: Amsterdam, 1984.

We claim:

1. A synthetic molecularly imprinted co-polymer prepared by steps consisting essentially of:
   copolymerizing (i) at least one monomer providing the synthetic molecularly imprinted copolymer with a free amide group, and (ii) at least one crosslinker, in the presence of (i) at least one polar organic solvent, and (ii) an enantiomer print molecule optionally having carboxylic acid functionality to form a co-polymerized composition;
   substantially removing from the co-polymerized composition the enantiomeric print molecule to form the synthetic molecularly imprinted co-polymer;
   wherein the print molecule, the monomer providing free amide, and the crosslinker are provided in a ratio sufficient to form specific noncovalent binding sites for the print molecule in the molecularly imprinted copolymer;
   and wherein the molecularly imprinted copolymer exhibits toward racemic mixtures of the enantiomer print molecule in polar solvent an enantiomeric separation factor alpha of at least 2.03.

2. A synthetic molecularly imprinted co-polymer according to claim 1, wherein the alpha value is at least 2.36.

3. A synthetic molecularly imprinted co-polymer according to claim 1, wherein the alpha value is at least 2.86.

4. A synthetic molecularly imprinted co-polymer according to claim 1, wherein the alpha value is at least 3.24.

5. A synthetic molecularly imprinted co-polymer according to claim 1, wherein the alpha value is at least 3.62.

6. A synthetic molecularly imprinted co-polymer according to claim 1, wherein the alpha value is at least 4.00.

7. A synthetic molecularly imprinted co-polymer according to claim 1, wherein the alpha value is sufficiently high to provide baseline resolution.

8. A synthetic molecularly imprinted co-polymer according to claim 1, wherein the enantiomeric resolution R is at least 1.58.

9. A synthetic molecularly imprinted co-polymer according to claim 1, wherein the enantiomeric resolution R is at least 1.73.

10. A synthetic molecularly imprinted co-polymer according to claim 1, wherein the enantiomeric resolution R is at least 1.88.

11. A synthetic molecularly imprinted co-polymer according to claim 1, wherein the enantiomeric resolution R is at least 2.02.

12. A synthetic molecularly imprinted co-polvmer according to claim 1, wherein the enantiomeric resolution R is at least 2.24.

13. A synthetic molecularly imprinted co-polymer according to claim 1, wherein the enantiomeric resolution R is at least 2.52.

14. A synthetic molecularly imprinted co-polymer according to claim 1, wherein the enantiomeric resolution R is at least 2.63.

15. A synthetic molecularly imprinted copolymer according to claim 1, wherein enantiomeric separation factor alpba is at least 2.86 and the enantiomeric resolution R is at least 2.63.

16. A synthetic molecularly imprinted copolymer according to claim 1, wherein enantiomeric separation factor alpba is at least 3.68 and the enantiomeric resolution R is at least 2.24.

17. A synthetic molecularly imprinted co-polymer according to claim 1, wherein the print molecule is an amino acid derivative.

18. A synthetic molecularly imprinted co-polymer according to claim 1, wherein the print molecule has carboxylic acid finctionality.

19. A synthetic molecularly imprinted co-polymer according to claim 1, wherein the crosslinker is a difunctional crosslinker.

20. A synthetic molecularly imprinted co-polymer according to claim 1, wherein the molar ratio of print molecule to amide monomer to crosslinker is about 1:4:20.

21. A synthetic molecularly imprinted co-polymer according to claim 1, wherein the ratio of print molecule to amide monomer to crosslinker is about 1:2:20 to about 1:4:20.

22. A synthetic molecularly imprinted co-polymer according to claim 1, wherein the molar ratio of print molecule to amide monomer to crosslinker is about 1:2:20.

23. A synthetic molecularly imprinted co-polymer according to claim 1, wherein the molar ratio of print molecule to amide monomer to crosslinker is about 1:4:20.

24. A synthetic molecularly imprinted co-polymer according to claim 1, wherein the polar solvent is acetonitrile, chloroform or water.

25. A synthetic molecularly imprinted co-polymer according to claim 1, wherein the polar solvent is acetonitrile.

26. A synthetic molecularly imprinted co-polymer according to claim 1, wherein the print molecule comprises amino acid.

27. A synthetic molecularly imprinted co-polymer according to claim 1, wherein the cross-linking component is ethylene glycol dimethacrylate.

28. A method for producing a synthetic molecularly imprinted copolymer consisting essentially of the steps of:
   copolymerizing (i) at least one monomer providing the synthetic molecularly imprinted copolymer with a free amide group, and (ii) at least one crosslinker;

in the presence of (i) at least one polar organic solvent, and (ii) an enantiomer print molecule optionally having carboxylic acid functionality, to form a co-polymerized composition;

substantially removing from the co-polymerized composition the enantiomeric print molecule to form the synthetic molecularly imprinted copolymer;

wherein the print molecule, the monomer providing free amide, and the crosslinker are provided in a ratio sufficient to form specific noncovalent binding sites for the print molecule in the molecularly imprinted copolymer;

and wherein the molecularly imprinted copolymer exhibits toward racemic mixtures of the enantiomer print molecule in polar solvent an enantiomeric separation factor alpha of at least 2.03.

29. A method according to claim 28, wherein the optional carboxylic acid functionality is present.

30. A method of separating an enantiomeric mixture comprising the step of:

passing an enantiomeric mixture through a separation medium comprising the synthetic molecularly imprinted composition according to claim 1.

31. A method according to claim 30, wherein the optional carboxylic acid functionality is present.

* * * * *